United States Patent [19]

Nakajima et al.

[11] Patent Number: 5,891,099
[45] Date of Patent: Apr. 6, 1999

[54] DISPOSAL MEDICAL THRUST DEVICE

[75] Inventors: Hiroaki Nakajima, Tokyo; Akihiro Higashiinoue, Miyazaki-ken, both of Japan

[73] Assignee: Togo Medikit Co., Ltd., Tokyo, Japan

[21] Appl. No.: 819,627

[22] Filed: Mar. 17, 1997

[30] Foreign Application Priority Data

Jul. 3, 1996 [JP] Japan .................................. 8-192981

[51] Int. Cl.⁶ .................................................. A61M 5/178
[52] U.S. Cl. ............................................ 604/167; 604/164
[58] Field of Search ................................... 604/161, 162, 604/164, 171, 192, 195, 198, 263, 167

[56] References Cited

U.S. PATENT DOCUMENTS

| 4,417,887 | 11/1983 | Koshi ....................................... 604/162 |
| 4,747,831 | 5/1988 | Kulli ........................................ 604/198 |
| 5,147,309 | 9/1992 | Hemmerich et al. ................... 604/192 |
| 5,156,599 | 10/1992 | Ranford et al. ......................... 604/198 |
| 5,232,450 | 8/1993 | Green et al. ............................ 604/164 |
| 5,573,510 | 11/1996 | Isaacson .................................. 604/164 |
| 5,665,072 | 9/1997 | Yoon ....................................... 604/164 |

FOREIGN PATENT DOCUMENTS

| 64-52480 | 2/1989 | Japan . |
| 1-136665 | 5/1989 | Japan . |
| 3-191965 | 8/1991 | Japan . |
| WO 8905392 | 6/1989 | WIPO ..................................... 604/164 |

Primary Examiner—Corrine M. McDermott
Assistant Examiner—Sharon Finkel
Attorney, Agent, or Firm—Nikaido, Marmelstein, Murray & Oram LLP

[57] ABSTRACT

Disclosed is an improved medical device comprising: a needle assembly comprising a needle body having a needle hub fixed to its needle; a hollow casing at least opening at its top for slidably containing the needle assembly, the opening top of the hollow casing having inward projections on its inner circumference; a stopper movably attached to the vicinity of the opening top of the hollow casing; and a protection cover for enclosing at least the sharp point of the needle, thereby permitting the needle assembly to be retained in the hollow casing by putting the stopper in the shutting position, or permitting the needle assembly to appear from the hollow casing by holding the needle hub of the inner needle between the inward projections of the opening top and the stopper, which is put in the shutting position. The inner needle can be retained in the casing or protection cover after removing it from the thrust spot, and the casing or protection cover containing the bacilli-contaminated needle therein can be thrown away as a disposable object.

9 Claims, 7 Drawing Sheets

DISPOSAL MEDICAL THRUST DEVICE

BACKGROUND OF THE INVENTION

1. Field of the Invention

The present invention relates to a medical thrust device such as an indwelling device or a syringe which is designed to subcutaneously its needle into the blood vessel or bile duct for injection or removal of blood or body fluids, and more particularly to a disposal medical device which is intended to be used once and then thrown away, thereby guaranteed to be free of contagion by injuring one's hand with the blood-smeared or bacilli-contaminated needle.

2. Description of Related Art

Such a disposal medical device includes a hard metal needle. A used needle is smeared with blood or body flood, which contains bacilli. Lest people should be infected with such bacilli, the blood-smeared needle body is used once and then thrown away. The precaution must be taken against every possible infection to doctors, nurses, assistants and collectors of waste materials. Therefore, the used needles must be contained in disposable casings, and advantageously the needle casings from which the needles are taken out are reused as such disposable casings.

Once a used needle has been put in its casing there will be no fear for infection. When the used needle is being put in the casing with one hand holding the used needle and with the other hand holding the casing, the person often injures his hand with the sharp point of the bacilli-contaminated needle.

In an attempt to prevent this dangerous incident, an indwelling device has been designed to have a needle cover responsive to removal of the needle from the spot for automatically covering its sharp point, as for instance in Japanese Patent 3-191965(A). Specifically, the needle cover is in the form of expandable-and-shrinkable (telescoping or coiled-spring) body, and it has a cap on its top end, and its bottom end is attached to the hub of the needle, and the cap is fixed to the hub of the surrounding cannula. The sharp point of the needle is allowed to appear from the cannula by shrinking the expandable-and-shrinkable body, and then the needle is thrusted into a selected part of the human body. As the needle is removed from the spot, the expandable-and-shrinkable body is allowed to expand so that the cap may cover the sharp point of the needle upon complete removal of the needle from the indwelling cannula.

The expandable-and-shrinkable body is maintained in the shrinking position only by the friction between the expandable-and-shrinkable body and the surrounding cannula, and also by the friction between the needle and the surrounding expandable-and-shrinkable body, and therefore, once the expandable-and-shrinkable body has been put in the shrinking position it may be possible to allow the expandable-and-shrinkable body along with the surrounding cannula to extend beyond the sharp point of the needle before or during rather than removal from the thrust spot. Thus, extra caution is required in use.

The expandable-and-shrinkable body must be long enough to cover the full length of the needle when it extends to its full length, and therefore, the radial size of the expandable-and-shrinkable body of telescoping type will be large. In case that the needle has a relatively long length, the outer radial size of the telescoping body when shrinked will be inhibitably large, radially extending a substantial size beyond the radial size of the cannula, thus causing an inconvenience in thrusting the needle into a selected part of the human body.

Further, there has been proposed an injection needle storing container designed to have a long pore having a broad part and a narrow part on a cover plate of the container for removing a injection needle from a syringe body by hooking the needle hub with the pore, for instance in Japanese Patent 1-52480(A) and 1-136665(A). A used injection needle is inserted into the broad part of the pore and shifted to the narrow part keeping a flange of the needle hub lower side of the cover plate and the syringe body is shifted upward to drop and store the separated injection needle into the container.

However, the used injection is exposed without cover before disposing into the container and accordingly it is not enough to guarantee to be free from infection. Also, it is afraid that long term storing may cause an accident to fall the container and the stored needles spring out of the hole.

Therefore, there has been an ever increasing demand for a disposal medical device guaranteed to be free of injuring one's hand with the bacilli-contaminated needle, still assuring that it can be handled with ease.

SUMMARY OF THE INVENTION

One object of the present invention is to provide a disposal medical device comprising a casing having at least an opening top with inner projections formed inside, a needle assembly slidably fitted in the casing, a stopper movable between an opening position and a shutting position and a protection cover for enclosing at least a sharp point of the needle, in which the hollow space of the casing is shut at least partly to separate into the forward, shortened and rearward, extended hollow sections.

The needle assembly can be selectively put by the stopper in a first, self-containing position in which the needle assembly is contained in the rearward, extended hollow section of the casing with the stopper in the shutting position, or in a second, thrusting position in which the needle appears from the casing with the rear hub of the needle assembly caught between the inner projections of the opening top of the casing and the stopper, which is put in the opening position. In case of indwelling devices they are usually in the first, self-containing position for circulation in market and storage in warehouses, and the devices will be put in the second, thrusting position for use.

In the thrusting position in which the needle appears from the opening top of the casing, the substantial length of the device is allotted to the holding of the device with one hand, thus facilitating the handling of the device. When thrusting is completed and the needle is removed from the cannula, the stopper is put in the opening position, thereby allowing the needle to fall in the casing or the protection cover to be contained and prevented from projecting from the casing by the stopper, which is now put in the shutting position. Thus, the device can be used once and then thrown away safely without fear of injuring one's hand with the bacilli-contaminated needle.

Additionally the device may use a protection cover to cover at least the sharp point of the needle, thereby preventing the injuring of one's hand prior to use by permitting the uncovering of the sharp point of the needle just prior to thrust.

The protection cover is press-fitted on the hub of the cannula or on the forward end of the hollow casing, thus enclosing the needle assembly. In case that the needle assembly is allowed to appear from the casing while being shipped, circulated in the market or stored in warehouses, the protection cover will prevent the exposing of the sharp point of the needle. Thus, the protection cover works as a needle case in shipping, circulating in the market or being warehoused, whereas the casing works as a disposable case after use. Advantageously the casing may be of a telescoping structure, and then it can be extended to contain the bacilli-contaminated needle when thrown away. Prior to use it can be shrinked to a shortened size, thereby reducing a substantial dead space which otherwise, would be occupied by the indwelling device in shipping, circulation in the market or storage in warehouses.

In place of using a relatively large-sized casing as a disposable container a relatively small-sized disposable case may be used. Then, the hub of the needle assembly may be composed of a head hub-section and a tail hub-section. The head hub-section is sized so as to permit it to pass through the reduced space defined by the inward projections of the opening top of the casing whereas the tail hub-section is sized so as to prevent it from passing through the reduced space of the top opening. The tail hub-section and the casing are equipped with anti-rotation means, and likewise, the head hub-section and the disposable case are equipped with anti-rotation means. After the bacilli-contaminated needle is allowed to fall in the casing, the disposable case is fitted on the needle assembly to cover the same, and then the disposable case is rotated to separate the needle-and-head hub-section from the tail hub-section, thus permitting the disposable case, which covers the needle and the head hub-section, to be removed from the casing and thrown away. Thus, the bacilli-contaminated needle can be thrown away safely as a relatively small-sized waste material. The protection tube may be sized and used as a disposable case.

The stopper is designed to reciprocate between the opening and shutting position, but it can be designed to move only in one direction from the shutting position to the opening position.

The invention may be applied to syringes, in which the hollow casing is made opened at its bottom to allow insertion of syringe body therefrom. The protection cover is made closing at the top and the opening bottom end is made detachable to each of the forward and rear end of the hollow casing, respectively. The stopper may have an additional small through hole for the injection nozzle of the syringe to be inserted therethrough.

In this case the needle assembly is allowed to appear from the casing being enclosed by the protection cover while being shipped, circulated in the market or stored in warehouses, thereby the protection cover works as a needle case not only in shipping, circulating in the market or being warehoused but also works as a disposable case after use in the form of being connected to the rear end of the hollow casing.

Other objects and advantages of the present invention will be understood from the following description of indwelling thrust devices according to preferred embodiments of the present invention, which are shown in accompanying drawings.

DESCRIPTION OF THE PREFERRED EMBODIMENTS

Figure 1:
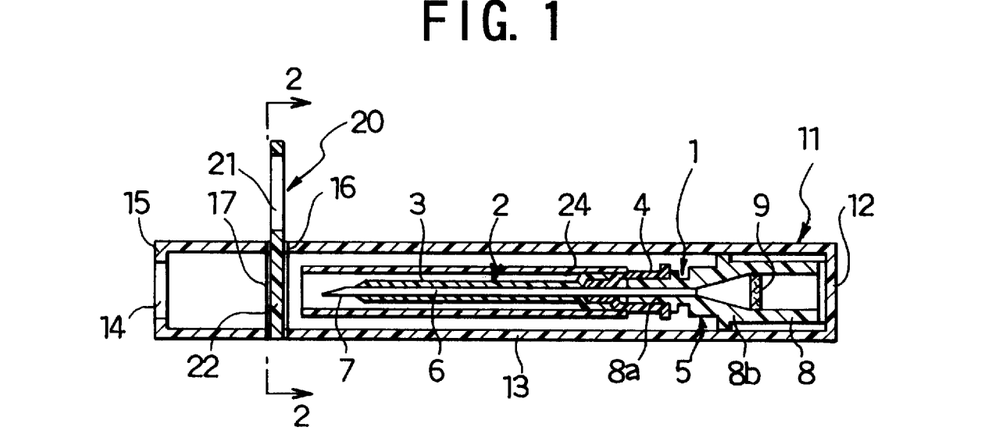
FIG. 1 is a longitudinal section of an indwelling type device according to a first embodiment.
Figure 2:
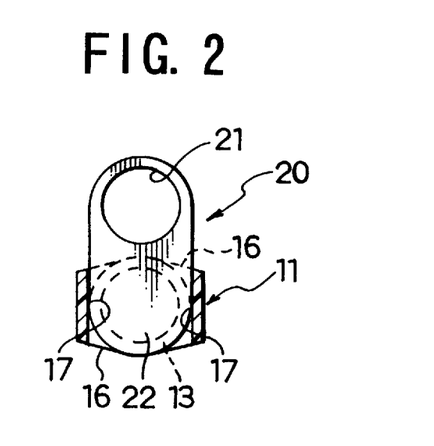
FIG. 2 is a cross section of the device taken along the line 2—2 in FIG. 1.

FIGS. 1 to 10 show indwelling type devices according to different embodiments of the present invention. Every indwelling thrust includes a needle assembly 1 comprising an indwelling cannula body 2 and a needle body 5. The indwelling cannula body 2 comprises a cannula 3 of a soft synthetic resin material, having a hard cylindrical hub 4 integrally or separately connected to its base end, and the needle body 5 comprises a metal needle 6 fitted in the indwelling cannula 3. The metal needle 6 has a sharp point 7 at one end and a hard synthetic resin hub 8 attached to the other end. The structure described so far is well known. Referring to FIG. 1, the hub 8 of the metal needle 6 is composed of a tapered head-section 8a of relatively small diameter and a tail-section 8b of relatively large diameter. The metal needle 6 is inserted in the cannula 3 with its sharp point 7 appearing therefrom. The tail hub-section 8b is loaded with a filter 9, which permits the passing-through of air, but prevents the passing-through of blood or other body fluids.

A casing 11 is an elongated hollow cylinder of a hard synthetic resin material, having a closed bottom 12 and an opening top 14. The opening top 14 has inward projections 15 formed on its inner circumference 13. Also, the hollow cylinder 11 has opposite guide slots 16 formed inside in a plane perpendicular to the axis of the hollow cylinder 11 in the vicinity of the opening top 14. A round-sided rectangular stopper plate 20 has a hole 21 formed close to one side, and the hole 21 has a diameter almost equal to the inner diameter of the casing 11. The stopper plate 20 is slidably inserted in the opposite guide slots 16 of the hollow cylinder 11 so as to move between the shutting position in which the closing wall section 22 of the stopper plate 20 closes the casing 11 in the vicinity of the opening end 14 and the opening position in which the hole 21 of the stopper plate 20 is put in alignment with the longitudinal hollow space of the casing 11.

The stopper plate 20 is positioned so as to separate the full length of the longitudinal hollow space of the casing 11 into the tail-section which is somewhat longer than the length of the indwelling needle assembly 1 and the head-section which is long enough to hold the tail hub-section 8b of the needle hub 8 tightly between the closing wall section 22 of the stopper plate 20 and the inward projections 15 of the opening top of the casing 11.

Figure 3A:
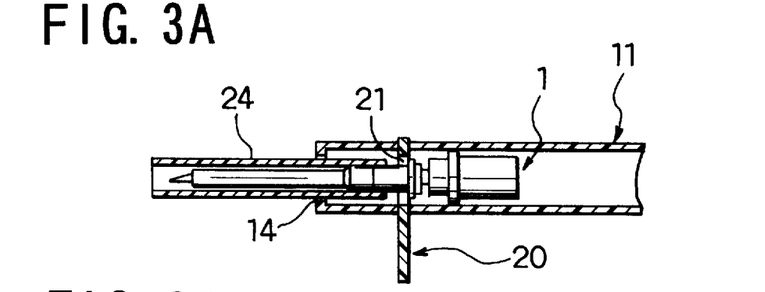
FIGS. 3A, 3B, 3C and 3D show how the device can be used.
Figure 3B:
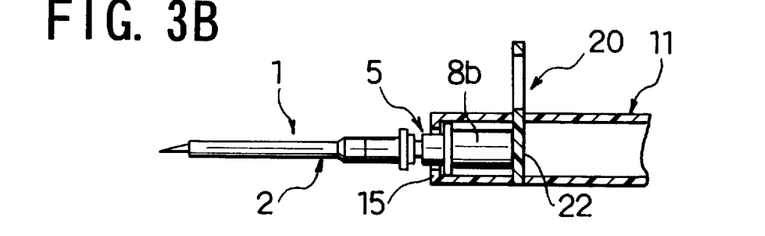
Figures 3C, 3D:
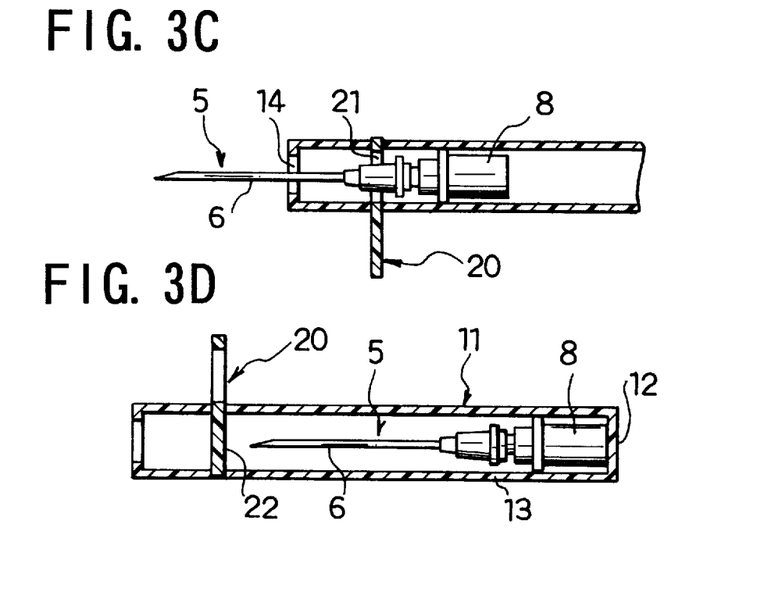

As seen from FIGS. 1 and 3, the indwelling thrust device according to the first embodiment has a protection cover 24 of hard synthetic resin press-fitted on the cannula hub 4. The protection cover 24 encloses the cannula 3 to extend a short distance beyond the sharp point 7 of the needle 6.

As seen from FIG. 1, the needle assembly 1 is put in the casing 11 with the needle hub 8 sitting on the bottom wall 12 of the casing 11, and the stopper plate 20 is put in the shutting position. The indwelling device when put in this position can be shipped, warehoused or circulated in the market.

In use, the stopper plate 20 is moved to the opening position, and then it is turned with its opening end 14 down, thereby allowing the needle assembly 1 to fall down by gravity, passing through the hole 21 of the stopper plate 20 and the reduced space defined by the inward projections 15 of the opening top 14 of the casing 11, as shown in FIG. 3(A). The hole 21 of the stopper plate 20 and the longitudinal hollow space of the casing 11 are somewhat larger than the tail hub-section 8b of the needle hub 8, thereby allowing the needle assembly 1 to fall slowly in the casing 11, or preventing the quick falling of the thrust needle assembly 1.

When the tail hub-section 8b of the needle hub 8 is caught by the inward projections 15 of the opening top 14 of the casing 11, the stopper plate 20 is put in the shutting position, thereby holding the tail hub-section 8b of the needle hub 8 between the closing wall section 22 of the stopper plate 20 and the inward projections 15 of the opening top of the casing 11. Then, the protection cover 24 is removed so that the indwelling device may be ready for use, as shown in FIG. 3(B).

The person holds the indwelling device by pinching the cannula hub 4 with thumb and index finger and by holding the casing 11 with the other fingers or otherwise, by gripping the casing 11 with all fingers, and he thrusts the sharp point of the needle into a selected part of the human body. The stopper plate 20 extends a short distance from the casing 11 in one direction, thus causing no hindrance to thrusting operation.

After the needle body 5 is removed from the thrust spot, leaving the cannula body 2 behind, the stopper plate 20 is put in the opening position in which the head-section communicates with the tail-section of the casing 11, and then the casing 11 is turned upright with its opening top 14 up, thus allowing the needle body 5 to fall slowly onto the bottom wall 12 of the casing 11 through the top opening 14 and the hole 21 (see FIG. 3C).

When the needle body 5 is sit on the bottom wall 12 of the casing 11, the stopper plate 20 is put in the shutting position, thereby preventing the needle body 5 from slipping off from the casing 11 (see FIG. 3D).

The first embodiment described so far is defined in claims 1, 2 and 3. The casing 11 is advantageously used as a container for pre- and post-use of needle, thus permitting the bacillie-contaminated needle to be thrown away as a waste material without using another extra casing for that purpose. The indwelling device can be selectively put in either condition of permitting use or throwing-away of the device simply by moving and putting the stopper plate in the shutting or opening position, and by turning the device upside down or down side up, without requiring access to the bacilli-contaminated needle by one's hand.

Figure 4:
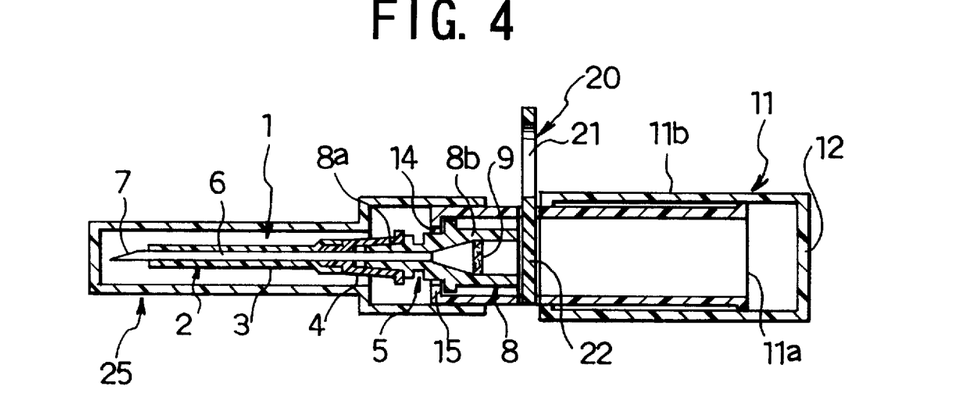
FIG. 4 is a longitudinal section of an indwelling type device according to a second embodiment.
Figure 5A:
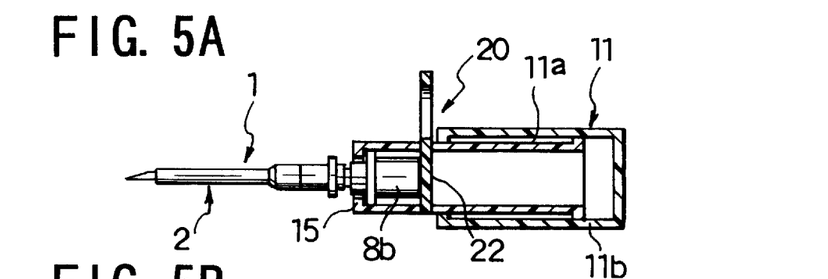
FIGS. 5A, 5B, 5C show how the device can be used.
Figure 5B:
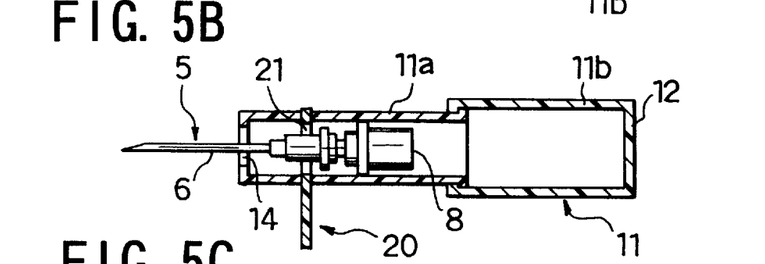
Figure 5C:
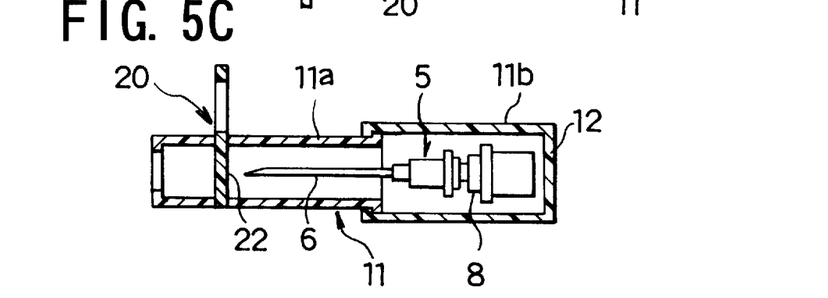

Referring to FIGS. 4 and 5, the indwelling device according to the second embodiment uses a protection cover 25 of hard synthetic resin, which protection cover 25 is press-fitted on the opening top 14 of the casing 11. The protection cover 25 is composed of head and tail cylindrical sections. The head cylindrical section has a relatively short diameter, and is closed at its top end, whereas the tail cylindrical section has a relatively long diameter, and is open at its bottom.

The needle assembly 1 is held by holding the tail hub-section 8b of the needle hub 8 between the closing wall section 22 of the stopper plate 20 and the inward projections 15 of the opening top 14 of the casing 11. The substantial length of the needle assembly 1 projecting from the casing is enclosed in the protection cover 25.

In this embodiment the needle assembly 1 projects from the casing 11, using the protection cover 25 as wrapping case. The casing 11 can be used as a disposable container. The casing 11 can be designed to be fixed or unadjustable in length as in the first embodiment, but advantageously it is designed to be adjustable in length. Specifically in order to reduce the whole size of the device to possible minimum when being shipped, warehoused or circulated in the market the casing 11 is of telescoping structure, and is composed of telescoping head- and tail-sections 11a and 11b. The head-section 11a is a bottomless hollow cylinder of relatively short diameter whereas the tail-section 11b is a bottomed hollow cylinder of relatively large diameter. The indwelling device can be shrinked by pushing the head-section 11a into the tail-section 11b when being shipped, warehoused or circulated in the market (see FIG. 4). When the device is used for the medical treatment, the protection cover 25 is removed to expose the substantial length of the thrust needle assembly (see FIG. 5A).

After the needle body 5 is removed from the thrust spot, leaving the cannula body 2 behind, the stopper plate 20 is put in the opening position in which the head-section communicates with the tail-section of the casing 11, and then the device is extended to its full length by pulling the tail-section 11b backward. Thereafter, the casing 11 is turned upright with its opening top 14 up, thus allowing the needle body 5 to fall slowly toward the bottom wall 12 of the casing 11 through the top opening 14 and the hole 21 (see FIG. 5B).

When the needle body 5 is sit on the bottom wall 12 of the casing 11, the stopper plate 20 is put in the shutting position, thereby preventing the thrust needle body 5 from slipping off from the casing 11 (see FIG. 5C). The indwelling device can be put easily in ready-for-use condition simply by removing the protection cover, and can be put in disposable condition by single-hand operation without requiring access to the bacilli-contaminated needle by hand.

The first embodiment uses a casing 11 large enough to contain the needle assembly 1, and the second embodiment uses an expandable casing 11 which can be extended to its full length to contain the bacilli-contaminated needle 6. Therefore, these embodiments are inevitably increased in size.

In an attempt to permit the size of the medical device to be reduced to possible minimum when being thrown away as a waste material a medical thrust device according to the third embodiment is so designed as to permit the protection cover to be used as a disposable container for the bacilli-contaminated needle. For that purpose the protection cover, needle hub and casing of the medical device according to the first embodiment are modified as described below.

Figure 6:
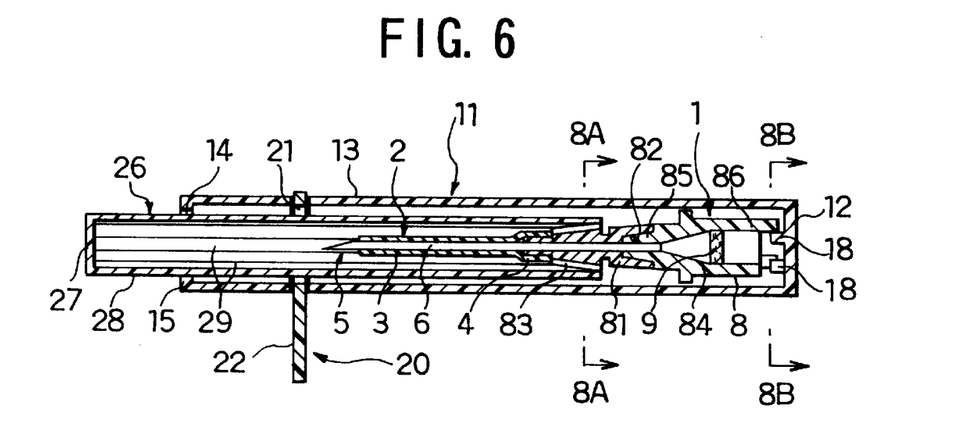
FIG. 6 is a longitudinal section of an indwelling type device according to a third embodiment.
Figure 7A:
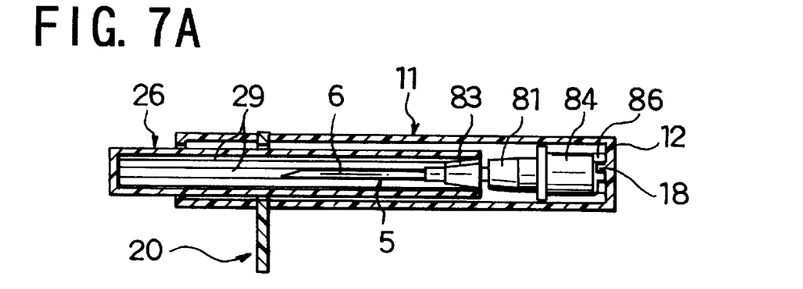
FIGS. 7A and 7B show how the device can be used.
Figure 7B:
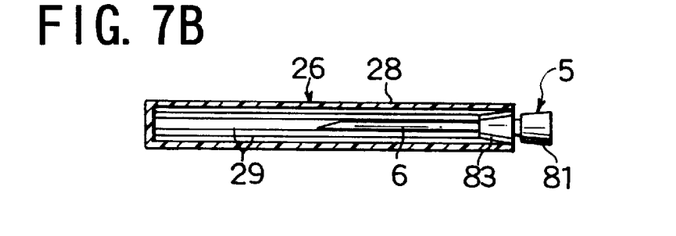
Figure 8A:
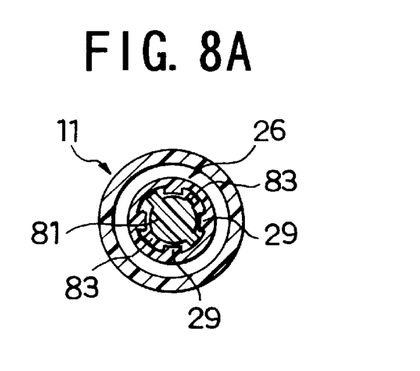
FIGS. 8A and 8B show enlarged cross sections of the device taken along the lines 8A—8A and 8B—8B in FIG. 6, respectively.
Figure 8B:
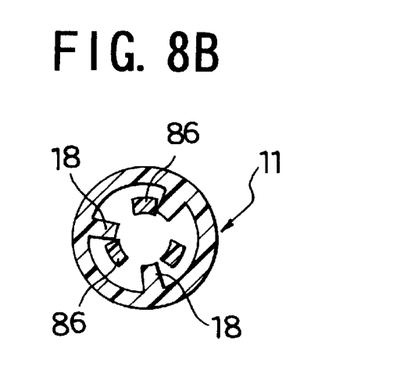

FIGS. 6, 7 and 8 show a medical device according to the third embodiment. As seen from FIG. 6, the needle hub 8 is composed of a head hub-section 81 and a tail hub-section 84. The tapering head hub-section 81 has longitudinal ribs 83 formed at regular intervals on its cone surface, and has the bottom end of the needle 6 press-fitted therein. As shown in FIG. 6, it has a tapering recess 82 made in its bottom. The tail hub-section 84 is detachably press-fitted in the bottom recess 82 of the head hub-section 81 at the tapering forward end 85. The head hub-section 81 is sized so as to pass through the reduced space defined by the inward projections 15 of the opening end 14 of the casing 11. The tail hub-section 84 has ribs 86 formed circumferentially at regular intervals on its bottom end. The tail hub-section 84 is sized so as to be caught by the inward projections 15 of the opening end 14 of the casing 11.

The protection cover 26 is an elongated hollow, bottomless cylinder of hard, synthetic resin, and is closed at its top by a top wall 27. It has longitudinal ribs 29 formed at regular intervals on its inner circumference, and is radially sized to be fit in the reduced space defined by the inward projections 15 of the opening top 14 of the casing 11. The casing 11 has ribs 18 circumferentially formed at regular intervals on the bottom wall 12.

As seen from FIG. 6, the protection cover 26 encloses the cannula 3 and the needle 6, and all of these parts are integrated together by press-fitting the bottom end of the protection cover 26 on the ribs 83 of the head hub-section 81 of the needle hub 8. The so integrated needle assembly 1 is inserted in the casing 11 until it has reached the bottom wall 12 of the casing 11, allowing the needle assembly 1 to partly appear from the opening top 14 of the casing 11 while being held tightly by the inward projections 15 of the opening top 14 of the casing 11. Thus, the medical device in this position can be shipped, warehoused or circulated in the market.

In use, the protection cover 26 is pulled out from the casing 11 until the tail hub-section 84 of the needle assembly 1 has been caught by the inward projections 15 of the opening top 14, and then, the stopper plate 20 is pushed to the shutting position to hold the tail hub-section 84 between the closing wall section 22 of the stopper plate 20 and the inward projections 15 of the opening top 14 of the casing 11, thus holding stably the needle assembly 1 at the top of the casing 11.

The protection cover 26 is removed so that the indwelling device may be ready for use. After the inner needle body 5 is removed from the thrust spot, leaving the cannula body 2 behind, the stopper plate 20 is put in the opening position in which the head-section communicates with the tail-section of the casing 11, and then the casing 11 is turned upright with its opening top 14 up, thus allowing the inner needle body 5 to fall slowly onto the bottom wall 12 of the casing 11 through the top opening 14 and the hole 21 of the stopper plate 20. This proceeding is similar to what is described with reference to FIGS. 3A, 3B and 3C.

When the inner needle body 5 is sit on the bottom wall 12 of the casing 11, the protection cover 26 is inserted into the casing 11 to press-fit its open bottom on the ribs 83 of the head hub-section 81 while rotating the protection cover 26, thus causing the longitudinal ribs 29 of the protection cover 26 and the hubs 86 of the tail hub-section 84 to engage with the ribs 83 of the head hub-section 81 and the ribs 18 of the bottom wall 12, respectively (see FIG. 7A). Then, the protection cover 26 is rotated along with the head hub-section 81 while the tail hub-section 84 is connected to the casing 11 so that the tail hub-section 84 remains still. As a result the tapering forward end 85 of the tail hub-section 84 is loosely fitted in the tapering recess 82 of the bottom of the head hub-section 81 so that the head hub-section 81 may be separated from the tail hub-section 84 (see FIG. 7B).

The protection cover 26 is positively connected by permitting the ribs 83 of the head hub-section 81 to cut in the inner circumference of the protection cover 26, thereby integrally connecting the head hub-section 81 to the protection cover 26. Then, the protection cover 26 holding the needle assembly therein is removed from the casing 11 to be thrown away as a disposable waste.

The medical device according to the third embodiment permits the protection cover 26 to be used as a disposable case for throwing the bacilli-contaminated needle away. The protection cover 26 is relatively small in size, accordingly reducing the amount of waste material. As described earlier, the bacilli-contaminated needle is allowed to fall in the casing 11, and the protection cover 26 is inserted into the casing 11 to cover the bacilli-contaminated needle. Therefore, there is no fear for injuring one's hand with the sharp point of the bacilli-contaminated needle in throwing away the dangerous object.

The medical devices according to the first, second and third embodiments of the present invention are appropriate for the needle of standard length. The size of these devices, particularly of their casings or protection covers will increase inhibitably with the increase of the needle length beyond 15 centimeters.

Figure 9:
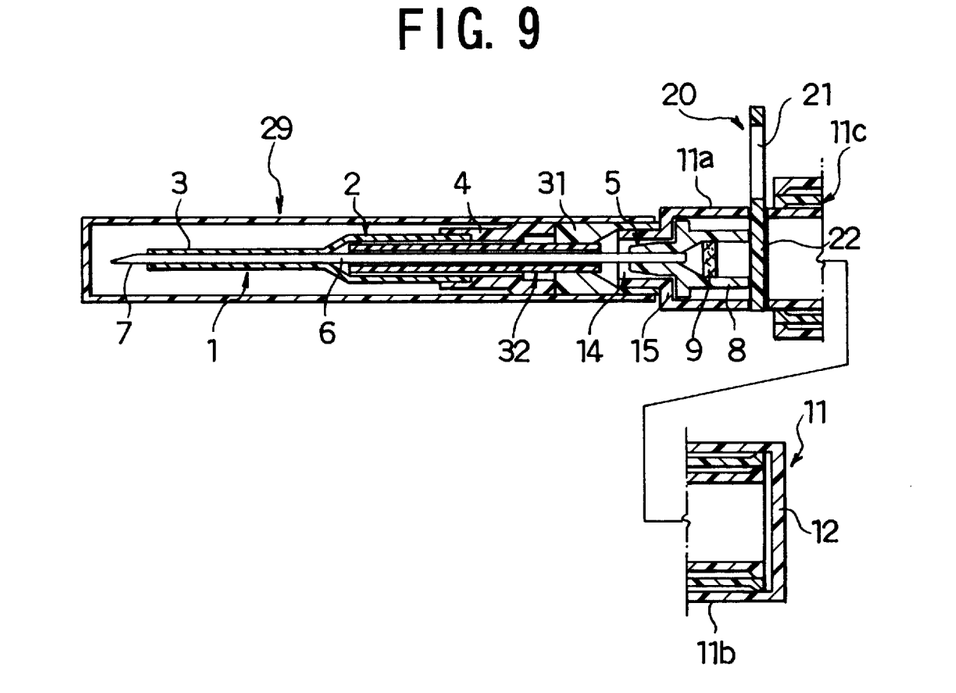
FIG. 9 is a longitudinal section of an indwelling type device according to a fourth embodiment.
Figure 10:
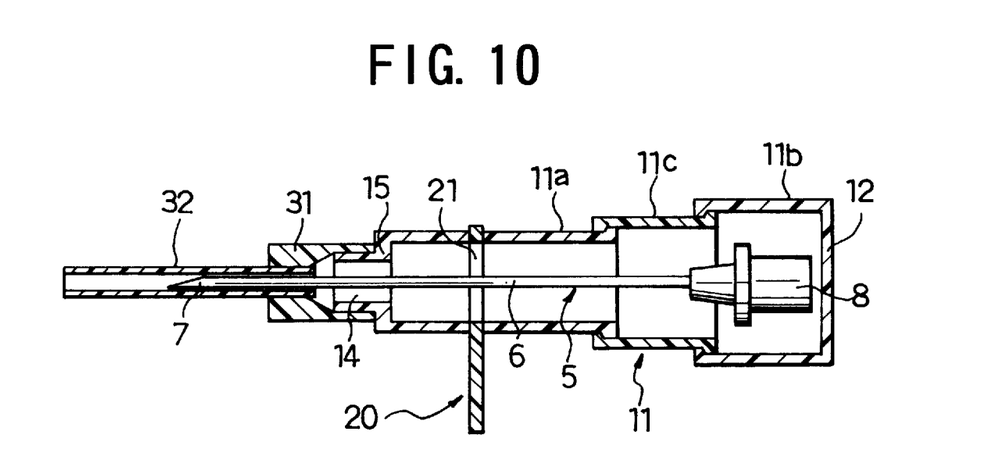
FIG. 10 shows how the device can be used.

In an attempt to reduce a disposable casing in size even if it is used in throwing away a relatively long needle after use, a medical device is designed according to the fourth embodiment as shown in FIGS. 9 and 10. It uses a three-sectioned telescoping casing 11, which is composed of a cylinder section 11a of relatively small size, a cylinder section 11c of intermediate size and a cylinder section 11b of relatively large size. The cylinder section 11a has a stopper plate 20 movably attached thereto; the cylinder section 11c is open at its opposite ends; and the cylinder section 11b has a bottom wall 12. These three cylinder sections can be shortened by collapsing, and can be elongated by extending to the full length.

The telescoping casing 11 has an auxiliary cylinder 31 of hard, synthetic resin applied to its top, and likewise the auxiliary cylinder 31 has a protection tube 32 of hard, synthetic resin or metal applied to its top. The protection tube 32 is somewhat larger than a needle 6 in diameter.

The needle assembly 1 is made up by the needle 6 and the protection tube 32 along with a cannula 3, a cannula hub 4 and a needle hub 8. As seen from FIG. 9, the cannula 3 surrounds the head length of the needle 6, and the cannula hub 4 surrounds the tail end of the cannula 3 and the intermediate length of the protection tube 32. The needle hub 8 is press-fitted on the tail end of the needle 6. The needle hub 8 of the needle assembly 1 is tightly held between the inward projections 15 of the opening top 14 of the casing 11 and the closing section 22 of the stopper plate 20. As described above, the protection tube 32 surrounds the intermediate length of the needle 6, and the auxiliary cylinder 31 is press-fitted into the bottom end of the cannula hub 4 to surround the tail length of the protection tube 32. The cylinder section 11a is press-fitted in the opening bottom of the auxiliary cylinder 31.

A protection cover 29 is an elongated hollow cylinder of hard, synthetic resin, which is closed at its top, and is open at its bottom. The protection cover 29 is applied to the thrust needle assembly 1 by press-fitting the open bottom of the protection cover 29 on the bulge of the cannula hub 4 and the auxiliary cylinder 31. The three-sectioned telescoping casing 11 is collapsed to the shortest length, as shown in FIG. 9. The medical device having the needle assembly 1 covered with the protection cover 29 and with the telescoping casing collapsed can be shipped, warehoused or circulated in the market.

In use, the protection cover 29 is removed from the casing 11, thereby exposing the needle assembly 1 to be ready for use. The sharp point of the needle 6 is thrusted in a selected part of a human body, and then, the needle 6 is withdrawn to leave the cannula body 2 behind. The stopper plate 20 is put in the opening position, and at the same time, the cylinder sections 11b and 11c are pulled out. Then, the extended casing 11 is turned upright with its opening top 14 up. The needle body 5 is allowed to pass through the opening top 14, the hole 21 of the stopper plate 20, and to fall toward the bottom wall 12. As seen from FIG. 10, the total size of the auxiliary cylinder 31 and the protection tube 32 are so determined that the sharp point of the needle 6 may reach short of the top end of the protection tube 32 when the needle body 5 stands on the bottom wall 12 of the extended casing 11, thus permitting the throwing-away of the used device. The stopper plate 20 is moved toward the shutting position to bend the used needle 6, thereby preventing the slipping-off of the bacilli-contaminated needle from the casing in throwing away.

The medical thrust device can be put in ready-for-use condition simply by removing the protection cover 29. The radial size of the head length of the device is reduced to possible minimum by using the protection tube 32 of reduced diameter extending from the top end of the telescoping casing 11, thus permitting the use of elongated needle without substantially increasing the disposable volume of the device.

Different forms of stopper other than the round-ended rectangular plate can be used.

Figure 11A:
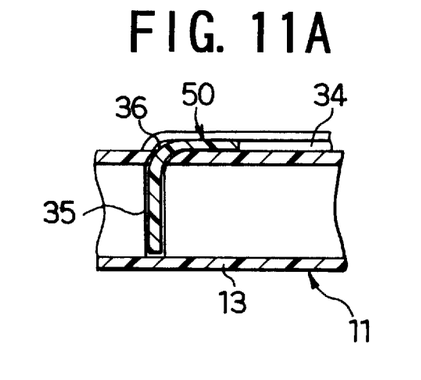
FIG. 11A is a longitudinal section of a selected part of an indwelling type devise.
Figure 11B:
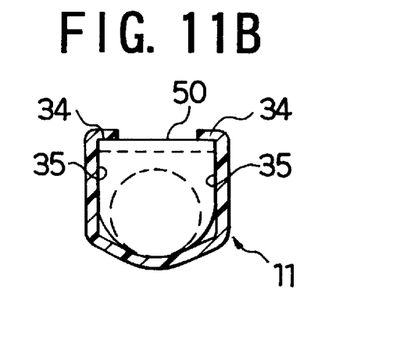
FIG. 11B is a cross section of the selected part of the device, showing a different form of stopper.

FIGS. 11A and 11B show a flexible, rectangular stopper plate 50 of soft synthetic resin, the opposite longitudinal sides of which rectangular stopper plate 50 are slidably fitted both in the opposite longitudinal guide slots 34 on the top side of the casing 11, and in the opposite vertical guide slots 35 on the inner, opposite lateral side walls of the casing 11.

The rectangular stopper plate 50 can be put selectively in opening or shutting position by pushing the stopper plate 50 backward or forward along the top surface of the casing 11.

Figure 12A:
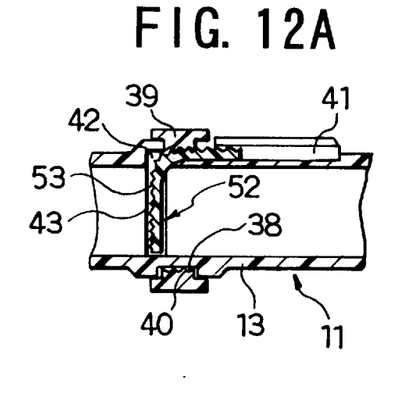
FIG. 12A is a longitudinal section of a selected part of an indwelling type device.
Figure 12B:
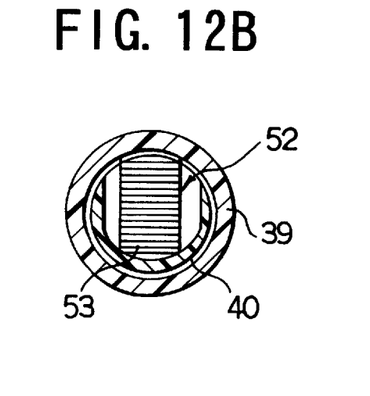
FIG. 12B is a cross section of the selected part of the device, showing another different form of stopper.

FIGS. 12A and 12B show another flexible, rectangular stopper plate 52 of soft synthetic resin, which has oblique threads 53 formed on its upper surface. An operating ring 39 is rotatably fitted in the circumferential slot 38, which is formed on the outer surface 13 of the casing 11. The operating ring 39 has spiral threads 40 formed inside, and these spiral threads 40 engage with the oblique threads 53 of the stopper plate 52. Opposite longitudinal guide slots 41 are formed on the top surface of the casing 11, and opposite vertical guide slots 35 are formed on the inner, opposite side walls of the casing 11. These longitudinal guide slots 41 and vertical guide slots 35 are continuous via a lateral slot 42, which is formed on the top surface of the casing 11. The opposite longitudinal sides of the rectangular stopper plate 52 are slidably fitted in the longitudinal guide slots 41 on the top surface of the casing 11, and in the vertical guide slots 35 on the inner, opposite side walls, passing through the lateral slot 42 of the casing 11.

The rectangular stopper 52 can move in and out of the hollow space of the casing 11 between the shutting position and the opening position.

These stopper plates can be used equally in medical devices according to the first, second, third and fourth embodiments described above, but a simpler stopper may be used in a medical device according to the fourth embodiment, in which the stopper need not be put in the shutting position to confine the needle in the casing.

Figure 13A:
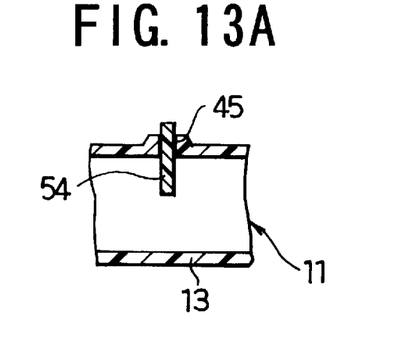
FIG. 13A is a longitudinal section of a selected part of an indwelling type device.
Figure 13B:
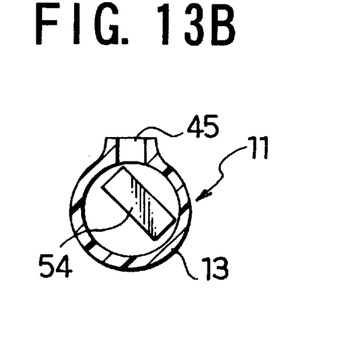
FIG. 13B is a cross section of the selected part of the device, showing still another different form of stopper.

FIGS. 13A and 13B show such a simple stopper 54, which is a rectangular plate of hard, synthetic resin. As shown in FIG. 13A, the rectangular plate 54 is fitted in the lateral slot 45, which is made in the ceiling of the casing 11. The rectangular plate 54 extends a mid distance in the hollow space of the casing 11 to hold the needle hub 8 of the needle assembly 1 between the stopper 54 and the inward projections 15 of the opening top 14 of the casing 11. The stopper 54 may be pushed in the hollow space of the casing 11, thereby confining the bacilli-contaminated needle in the casing to prevent it from slipping off from the casing 11. If the needle is long enough to extend beyond the stopper 54, the bacilli-contaminated needle can be bent by pushing the stopper 54 in the hollow space of the casing 11, thereby positively holding the used needle in the casing 11 to assure even more safety in throwing the disposable object away.

Figure 14:
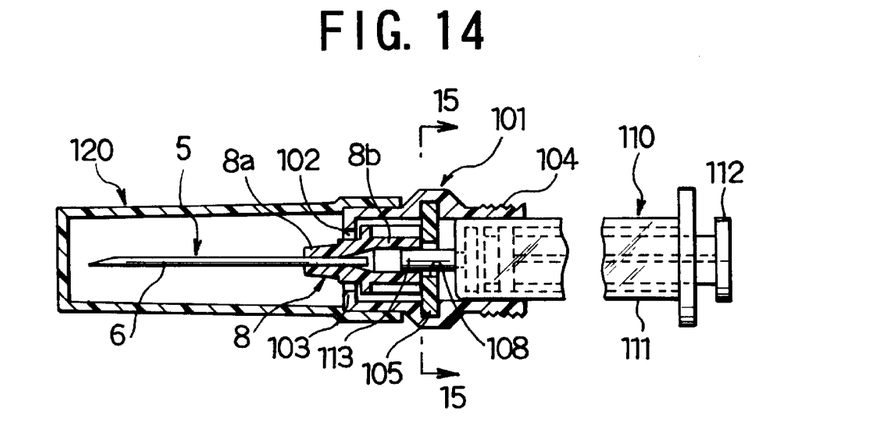
FIG. 14 is a longitudinal section of a syringe type device according to a fifth embodiment.
Figure 15:
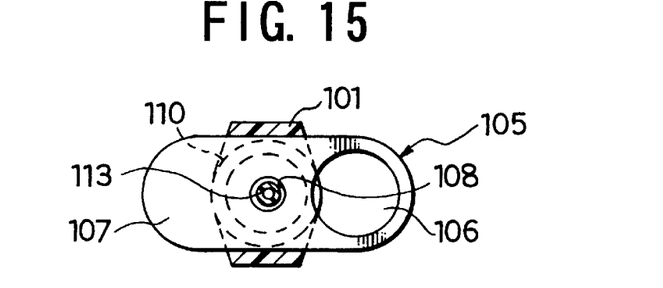
FIG. 15 is a cross section of the device taken along the line 15—15 in FIG. 14.

FIG. 14 shows a syringe type device according to a fifth embodiment of the present invention. The device in this embodiment uses a hollow casing 101 which is bottomless to allow insertion of a syringe 110 therethrough and is relatively short. The syringe 110 is composed with a hollow barrel 111 and plunger 112 slidably inserted into the hollow barrel. The hollow barrel 111 has a cylindrical connector 113 on its top end to be fitted into the needle hub 8 of the needle body 5. It uses a stopper 105 having an additional small through hole 108 between the hole 106 for the opening section and the closing wall section 107.

A protection cover 120 is press-fitted on the opening top 102 of the casing 101, and is closed at its top end. The needle body 5 is held by holding the tail hub-section 8b of the needle hub 8 between the the stopper plate 105 and the inward projections 103 of the opening top 102 of the casing 101, in which the connector 113 of the syringe 110 passes through the small through hole 108 of the stopper 105 to be fitted into the needle hub 8. The substantial length of the needle body 5 projecting from the casing is enclosed in the protection cover 120.

Figure 16A:
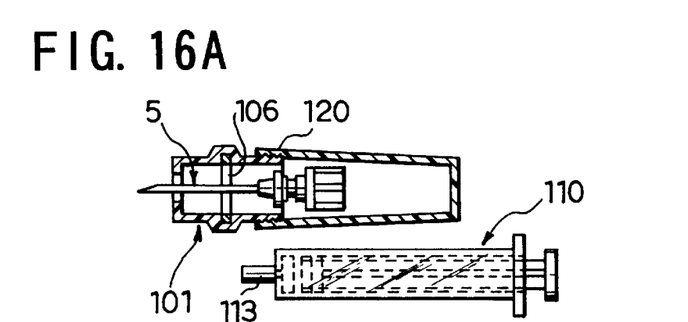
FIGS. 16A and 16B show how the device can be used.
Figure 16B:
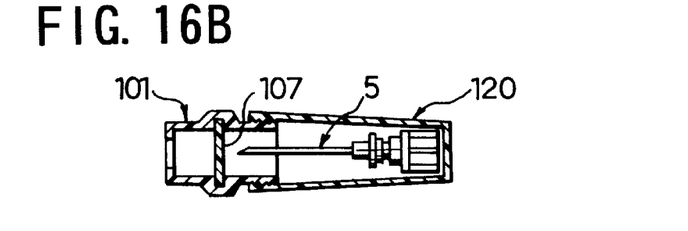

In this embodiment the protection cover 120 is used as wrapping case when being shipped, warehoused or circulated in the market (see FIG. 14). The protection cover 120 is used also as a disposable container together with the casing 101 by connecting the bottom opening end to the screwed rear end 104 of the casing 101 (see FIG. 16).

As may be understood from the above, a medical device according to the present invention is designed so as to permit the needle to be confined in its casing, and to permit the needle to appear from its casing, and also it is designed so as to permit its casing to be used as a disposable container, in which the used needle can be put in without fear of injuring one's hand with the sharp point of the bacilli-contaminated needle.

Also, it is designed so as to have a protection cover to enclose at least the sharp point of the needle, thereby guaranteed to be free of injuring people with the sharp point of the needle prior to thrust. The protection cover may be used as a disposable container.

The casing extends behind the needle in use, thus conveniently permitting the holding of the device by the casing with hand.

What is claimed is:

1. A medical device for intravenous delivery comprising:
    a needle assembly comprising a needle body having a needle hub fixed to its needle;
    a hollow casing having guide slots and at least an opening at its top for slidably containing the needle assembly completely within the casing, the opening top of the hollow casing having inward projections on its inner circumference;
    a stopper plate slidably attached to said guide slots of the hollow casing and separating an interior of said hollow casing into a forward section and a rearward section, the needle assembly being completely containable in said rearward section, the stopper plate being movable between an opening position and a shutting position at which the interior of the hollow casing is closed; and
    a protection cover for enclosing at least a sharp point of the needle,
    wherein the needle assembly can be completely retained in the rearward section of the hollow casing with the stopper plate in the shutting position, or the needle assembly can be extended from the hollow casing and held there by holding the needle hub of the needle between the inward projections of the opening top of the hollow casing and the stopper plate in the shutting position.

2. A medical device according to claim 1 wherein said needle assembly further comprises an indwelling cannula body having a cannula hub fixed to its cannula and detachably attached to the needle hub, the needle being covered with the cannula body, and wherein the hollow casing has a closed bottom.

3. A medical device according to claim 2 wherein the protection cover has means to detachably connect a bottom end thereof to the cannula hub while the needle assembly is retained in the hollow casing with the stopper plate in the shutting position.

4. A medical device according to claim 2 wherein the protection cover has a closed top and means to detachably connect a bottom end thereof to the forward end of the hollow casing while the needle assembly is extended from the hollow casing with the needle hub between the inward projections of the opening top of the hollow casing and when the stopper plate is put in the shutting position, thereby permitting the needle assembly extended from the hollow casing to be contained in the protection cover.

5. A medical device according to claim 4 wherein the hollow casing includes longitudinally telescoping cylindrical sections on an end opposite to the opening top thereof relative to the stopper plate.

6. A medical device according to claim 2 wherein the needle hub comprises a head hub-section and a tail hub-section, these hub-sections being detachable from each other, the head hub-section being sized so as to permit the passing of the head hub-section through the opening space defined by the inward projections of the opening top of the hollow casing, the tail hub-section being sized so as to prevent the passing of the tail hub-section through the opening space defined by the inward projections of the opening top, the protection cover being detachably connected to the head hub-section to enclose the needle assembly, the tail hub-section and hollow casing being equipped with anti-rotation means, and the head hub-section and the protection cover being equipped with rotation resistive means, the protection cover having the needle assembly contained therein being caught by the inward projections of the opening top of the casing to partly extend from the opening top of the hollow casing, while the stopper is in the opening position.

7. A medical device according to claim 2 further comprising a protection tube detachably attached to and extending from the opening top of the hollow casing, the protection tube enclosing the needle when the needle assembly is caught and held by the needle hub between the inward projections of the opening top of the hollow casing and the stopper plate when in the shutting position; and wherein the hollow casing includes longitudinally telescoping cylindrical sections on an end opposite to the opening top relative to the stopper plate.

8. A medical device according to claim 1 wherein said device is a syringe wherein the hollow casing is open at its bottom, the protection cover is closed at the top and has means to detachably connect a bottom end thereof to the forward and rear end of the hollow casing respectively, and wherein the syringe further comprises a syringe body having a hollow barrel and a plunger slidably fitted into the hollow barrel, the stopper plate having an additional small through hole to be passed through by a cylindrical connector at front of the hollow barrel to be connected to the needle hub, while the needle assembly extends from the hollow casing with the needle hub between the inward projections of the opening top of the hollow casing and the stopper plate, the needle assembly extended from the hollow casing being encased in the protection cover.

9. A medical device for intravenous delivery comprising:
    a needle assembly comprising a needle body having a needle hub fixed to its needle;
    a hollow casing having guide slots and at least an opening at its top for slidably containing the needle assembly, the opening top of the hollow casing having inward projections on its inner circumference;
    a stopper plate having an opening hole section and a closing wall section and being slidably attached to the guide slots of the hollow casing, the stopper plate being movable between an opened position in which said opening hole section is in alignment with the interior of said hollow casing and a closed position in which said wall section is in alignment with the interior of said hollow casing and the inner space of the hollow casing is closed; and
    a protection cover for enclosing at least a sharp point of the needle, wherein the needle assembly can be retained in the hollow casing by setting the stopper plate in the closed position, or the needle assembly can be extended from the hollow casing by holding the needle hub of the needle between the inward projections of the opening top of the hollow casing and the stopper plate when the stopper plate is set in the closed position.

* * * * *